United States Patent
Lee et al.

(10) Patent No.: US 8,969,084 B2
(45) Date of Patent: Mar. 3, 2015

(54) METHOD FOR DETECTING SWEET ODOR FROM AIR CONDITIONER, REPRODUCING SWEET ODOR AND PREPARING CORRESPONDING SWEET ODOR COMPOSITION

(71) Applicant: Hyundai Motor Company, Seoul (KR)

(72) Inventors: Tae Hee Lee, Gyeonggi-do (KR); Ji Wan Kim, Gyeonggi-do (KR); Seok Man Kim, Ulsan (KR); Sang Jun Lee, Gyeongsangnam-do (KR)

(73) Assignee: Hyundai Motor Company, Seoul (KR)

( * ) Notice: Subject to any disclaimer, the term of this patent is extended or adjusted under 35 U.S.C. 154(b) by 0 days.

(21) Appl. No.: 13/951,918

(22) Filed: Jul. 26, 2013

(65) Prior Publication Data
US 2014/0183412 A1 Jul. 3, 2014

(30) Foreign Application Priority Data

Dec. 31, 2012 (KR) .................. 10-2012-0157954

(51) Int. Cl.
G01N 33/00 (2006.01)
G01N 31/00 (2006.01)
B60H 1/00 (2006.01)
G01N 30/72 (2006.01)

(52) U.S. Cl.
CPC ........ *G01N 33/0009* (2013.01); *B60H 1/00585* (2013.01); *G01N 30/7206* (2013.01)
USPC ............... 436/9; 436/8; 436/128; 436/131; 436/132; 436/140; 436/141; 436/161; 436/173; 436/174; 252/372; 252/408.1; 73/23.34

(58) Field of Classification Search
USPC ......... 436/8, 9, 127, 128, 140, 141, 131, 132, 436/161, 173, 174; 252/372, 408.1; 73/23.2, 23.34
See application file for complete search history.

(56) References Cited

U.S. PATENT DOCUMENTS

| | | | |
|---|---|---|---|
| 2005/0191213 A1* | 9/2005 | Casillas et al. | 422/99 |
| 2010/0022437 A1* | 1/2010 | Artiga-Gonzalez et al. | 512/4 |
| 2014/0087471 A1* | 3/2014 | Lee et al. | 436/9 |
| 2014/0087475 A1* | 3/2014 | Lee et al. | 436/113 |

OTHER PUBLICATIONS

Yoshida et al. Indoor and Built Environment, vol. 15 (5), 2006, pp. 425-444.*
Kim et al. Journal of Chromatography A, vol. 1204, 2008, pp. 72-80.*
Kim et al., "A Study on odor evaluation of automobile air conditioner evaporator by using lab-scale test bench", Kangwon National University, pp. 685-691 (2006).
Lee, Tae-woong, "Evaluation of VOC and odor on car air conditioning evaporator with and without coating", Dept. of Environ. Sci. Grad. School, Kangwon National University.
Yu, Y.J. et al., "A Study on Mechanism and Identification of Odor-Active Compounds Emitted from Air Conditioning System Using TD/GC/TOF-MS/O", Dept. of Environ. Sci., KangWon National University.
Jae, Y.Y et al, "Investigation of Reproduction Method for Malodor Emitted from Automobile Air Conditioner and Identification of VOCs from Evaporator Using Test Cooling Bench", English translation, 3 pages.
Kim, Kyung Hwan et al., "A Study on Odor Evaluation of Automobile Air Conditioner Evaporator by Using Lab-Scale Test Bench", pp. 685-691 (2006) English Abstract.

* cited by examiner

*Primary Examiner* — Maureen Wallenhorst
(74) *Attorney, Agent, or Firm* — Mintz Levin Cohn Ferris Glovsky and Popeo, P.C.; Peter F. Corless

(57) ABSTRACT

A method that identifies the compounds contributing to a sweet odor from an air conditioner, reproduces the sweet odor, and prepares a corresponding sweet odor composition. Through the analysis method of the present invention, the compounds contributing to the sweet odor from an air conditioner are identified and quantified. The sweet odor is reproduced from a combination of the compounds identified by the analysis method of the present invention. The reproduced sweet odor provides significant data required for development of an apparatus and a method for removing specific odor.

8 Claims, 1 Drawing Sheet

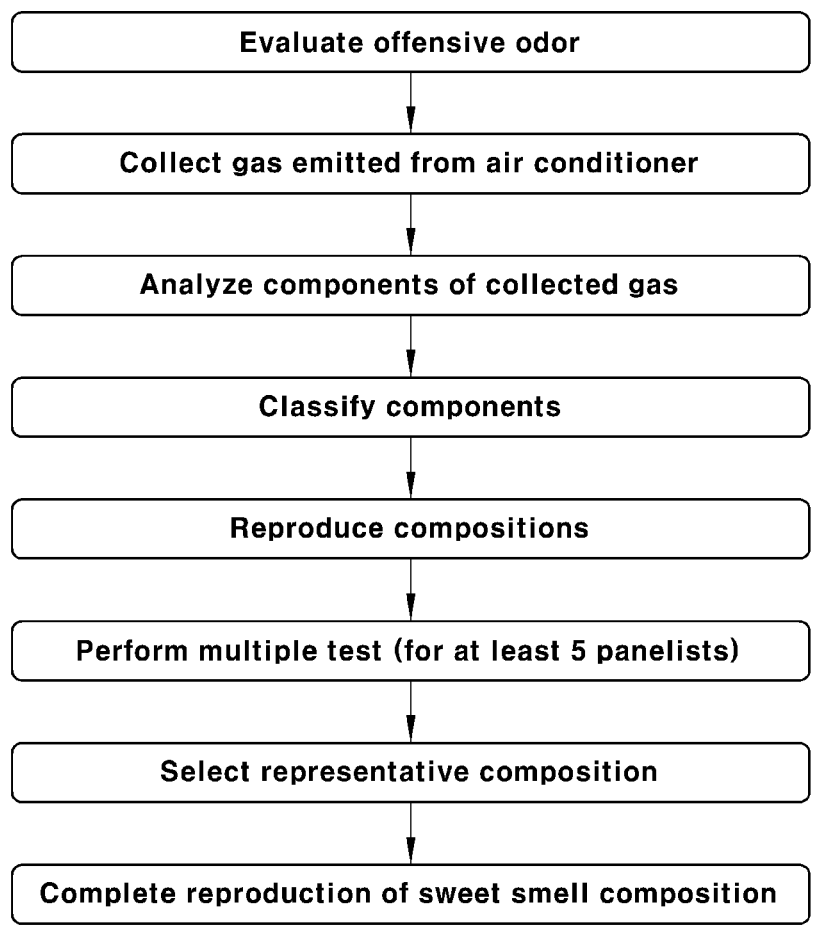

METHOD FOR DETECTING SWEET ODOR FROM AIR CONDITIONER, REPRODUCING SWEET ODOR AND PREPARING CORRESPONDING SWEET ODOR COMPOSITION

CROSS-REFERENCE TO RELATED APPLICATIONS

This application claims priority under 35 U.S.C. §119 to Korean Patent Application No. 10-2012-0157954, filed on Dec. 31, 2012 in the Korean Intellectual Property Office, the disclosure of which is incorporated herein by reference in its entirety.

BACKGROUND (a) Technical Field

The present invention relates to a method for detecting a combination of compounds contributing to sweet odor from an air conditioner, a method for reproducing the sweet odor and preparing a corresponding sweet odor composition.

(b) Background Art

Clean air is an essential element for the maintaining human health and well-being. Two important factors that lead to unsatisfactory interior air quality in an airtight building are the building itself producing a substantial amount of air pollutants that need to be removed or diluted; and odor generated as a result of human activities.

An air-cooling system lowers interior temperature and optimizes interior environment through air conditioning which changes air temperature, humidity, flow and cleanliness to more favorable conditions. Increasingly, air-cooling systems are being used to improve the standard of living. Although the air-cooling systems have been improved functionally over time, problems remain to be solved in terms of interior air quality. In the past, lowering interior temperature was viewed as one of the most fundamental and important functions of the air-cooling system. However, currently, health-related aspects such as interior air quality and odor may also be regarded as important functions of air-cooling systems. In particular, complaints regarding interior air quality include offensive odor such as sweet odor, foul odor, foot odor, and the like. To solve the odor problem, it may be necessary to analyze the odor-causing substances and understand the fundamental cause of the odor.

Fungal and bacterial metabolites have been known to be a main cause of odor from an air conditioner, however, the type and the amount of metabolites produced from the microorganisms may remain unclear. Additionally, since it is unclear specifically what compounds cause the offensive odor, it may be necessary to understand the type of compounds that contribute to the sweet odor from the air conditioner.

SUMMARY

Numerous complaints are commonly made regarding various offensive odors from an air conditioner (e.g., more than 20 types including musty odor). The present invention discloses a method for identifying the compounds contributing to sweet odor from an air conditioner, collecting offensive-smelling gas from a vehicle, and developing a method for artificially reproducing the sweet odor.

The present invention provides a method for detecting the compounds contributing to sweet odor from an air conditioner from among various offensive odors emitted from the air conditioner.

The present invention also provides a method for identifying the compounds contributing to sweet odor from an air conditioner from among various offensive odors emitted from the air conditioner and artificially reproducing the sweet odor using the identified chemical compounds. Additionally, the present invention provides a method of preparing a corresponding sweet odor composition from the detected sweet odor. The sweet odor composition may also be applicable to any applications where sweet odor is emitted, in addition to the air conditioner.

In an aspect, the present invention provides a sweet odor composition from an air conditioner including one or more compound selected from a group consisting of: hexanal, ethyl-2-methylbutyrate, heptanal, octanal, decanal, 1,3,5-trimethylbenzene, 1-methoxy-2-propanol, decane, 2-butoxyethanol, ethylbenzene, heptane, n-propylbenzene, 2-methylbenzene, n-undecane and n-tridecane.

In another aspect, the present invention provides a sweet odor composition from an air conditioner including: hexanal, ethyl-2-methylbutyrate, heptanal, octanal, decanal, 1,3,5-trimethylbenzene, 1-methoxy-2-propanol, decane, 2-butoxyethanol, ethylbenzene, heptane, n-propylbenzene, 2-methylbenzene, n-undecane and n-tridecane.

In yet another aspect, the present invention provides a method for analyzing the compounds contributing to sweet odor from an air conditioner, including the steps of:

(i) collecting a gas emitted from an air conditioner; and
(ii) analyzing the components of the gas.

In another aspect, the present invention provides a method for preparing a corresponding sweet odor composition from a detected sweet odor, including mixing two or more compounds selected from a group consisting of: hexanal, ethyl-2-methylbutyrate, heptanal, octanal, decanal, 1,3,5-trimethylbenzene, 1-methoxy-2-propanol, decane, 2-butoxyethanol, ethylbenzene, heptane, n-propylbenzene, 2-methylbenzene, n-undecane and n-tridecane.

BRIEF DESCRIPTION OF THE DRAWING

The above and other objects, features and advantages of the present invention will now be described in detail with reference to exemplary embodiments thereof illustrated in the accompanying drawing which is given hereinbelow by way of illustration only, and thus are not limitative of the invention, and wherein:

FIG. 1 is an exemplary flow chart describing a method for analyzing the compounds contributing to sweet odor according to an exemplary embodiment of the present invention.

DETAILED DESCRIPTION

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, fuel cell vehicles, combustion, plug-in hybrid electric vehicles, hydrogen-powered vehicles and other alternative fuel vehicles (e.g. fuels derived from resources other than petroleum).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Hereinafter, reference will now be made in detail to various exemplary embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the accompanying claims.

In an aspect, the present invention provides a sweet odor composition from an air conditioner including one or more compound selected from a group consisting of: hexanal, ethyl-2-methylbutyrate, heptanal, octanal, decanal, 1,3,5-trimethylbenzene, 1-methoxy-2-propanol, decane, 2-butoxyethanol, ethylbenzene, heptane, n-propylbenzene, 2-methylbenzene, n-undecane and n-tridecane. More specifically, the present invention provides a sweet odor composition from an air conditioner including: hexanal, ethyl-2-methylbutyrate, heptanal, octanal, decanal, 1,3,5-trimethylbenzene, 1-methoxy-2-propanol, decane, 2-butoxyethanol, ethylbenzene, heptane, n-propylbenzene, 2-methylbenzene, n-undecane and n-tridecane.

The sweet odor composition from an air conditioner may include: about 0.0001-0.01 ppm of hexanal; about 0.0001-0.01 ppm of ethyl-2-methylbutyrate; about 0.00007-0.007 ppm of heptanal; about 0.0001-0.012 ppm of octanal; about 0.0001-0.013 ppm of decanal; about 0.0004-0.04 ppm of 1,3,5-trimethylbenzene; about 0.0003-0.03 ppm of 1-methoxy-2-propanol; about 0.0003-0.03 ppm of decane; about 0.001-0.1 ppm of 2-butoxyethanol; about 0.0002-0.03 ppm of ethylbenzene; about 0.0004-0.05 ppm of heptane; about 0.00008-0.01 ppm of n-propylbenzene; about 0.00008-0.08 ppm of 2-methylbenzene; about 0.0004-0.05 ppm of n-undecane; and about 0.0001-0.015 ppm of n-tridecane.

In another aspect, the present invention provides a method for analyzing the compounds contributing to sweet odor from an air conditioner, including the steps of:
(i) collecting a gas emitted from an air conditioner; and
(ii) analyzing the components of the gas.

In another aspect, the present invention provides a method for analyzing the compounds contributing to sweet odor from an air conditioner and reproducing the sweet odor, including: evaluating offensive odor; collecting a gas emitted from an air conditioner; analyzing the components of the collected gas; classifying the components; reproducing compositions; performing a multiple test (for at least 5 panelists); selecting the representative composition; and completing the reproduction of the sweet odor composition.

FIG. 1 is an exemplary flow chart describing the method for analyzing the compounds contributing to sweet odor and reproducing the sweet odor.

The sweet odor from an air conditioner of the present invention may be from an air conditioner in an environment including a building, a vehicle, van, bus, etc. More specifically, the air conditioner may be an air conditioner used in a vehicle, van or bus.

In an exemplary embodiment of the present invention, the gas in (ii) may include hexanal, ethyl-2-methylbutyrate, heptanal, octanal, decanal, 1,3,5-trimethylbenzene, 1-methoxy-2-propanol, decane, 2-butoxyethanol, ethylbenzene, heptane, n-propylbenzene, 2-methylbenzene, n-undecane and n-tridecane. In addition, the concentration of the hexanal, ethyl-2-methylbutyrate, heptanal, octanal, decanal, 1,3,5-trimethylbenzene, 1-methoxy-2-propanol, decane, 2-butoxyethanol, ethylbenzene, heptane, n-propylbenzene, 2-methylbenzene, n-undecane and n-tridecane that contribute to the sweet odor may be measured. The analysis of the components in (ii) may be performed by gas chromatography/mass spectrometry (GC/MS), gas chromatography with atomic emission detector (GC/AED), gas chromatography/flame ionization detection/olfactometry (GC/FID/olfactometry) or high-performance liquid chromatography (HPLC), but is not necessarily limited thereto.

Representative examples of the analysis method of the present invention are described hereinbelow. However, the analysis method of the present invention is not limited thereto.

Gas Chromatography

In gas-solid chromatography (GSC), an adsorbent solid powder may be used as the stationary phase. In addition, in gas-liquid chromatography (GLC), a liquid stationary phase coated on a solid support may be used.

A carrier gas maintained at a constant flow rate may be supplied from a sample injection device into a separation column via a pretreatment apparatus and discharged after passing through a detector. The pretreatment apparatus, the sample injection device, the column and the detector may be maintained at predetermined temperatures.

When a gas or liquid is introduced into the sample injection device, the gas may be carried into the column by the carrier gas and the liquid may be carried into the column by the carrier gas after being heated and evaporated. The components of the sample may be separated in the separation column based on difference in absorption or solubility and may sequentially pass through a mass analyzer disposed at the outlet of the separation column.

The time between the injection of the sample into the separation column until a peak occurrence as a result of detection of a specific component included therein may be called retention time, and the retention time multiplied by the flow rate of the carrier gas may be called retention volume. Qualitative analysis may be performed on the process since the values of the retention time and volume may be different for different components under given experimental conditions. Furthermore, quantitative analysis may be conducted since the peak area or height may be related to the amount of the corresponding component present.

Electron ionization is a conventionally used ionization technique. Neutral sample molecules in gas state are bombarded with high-speed electrons to detach electrons and form molecular ions (cations, $M^+$). The minimum energy required to produce the molecular ion (M+) from the neutral molecule (M) may be called ionization energy (IE). The ionization energy of an organic compound is about 8-12 eV (800-1200 kJ/mol$^{-1}$).

$$M + e^- \rightarrow M^+ + 2e^-$$

Among the produced molecular ions, those with high internal energy may be fragmented to form fragment ions. To prevent ion formation as a result of reaction between the produced ion and the neutral molecule, the pressure inside the ionization source should be maintained at $10^{-5}$ torr or lower.

Electron beams emitted from a filament may be accelerated to 70 eV to obtain standard mass spectrums since they provide high ionization efficiency with little change in mass spectrum. The mass spectrum is the recording of the mass-to-charge ratio (m/z) of the molecular ions and the fragment ions. The mass spectrum of the unknown sample may be compared with the stored standard mass spectrums to identify the substance.

Electric fields and magnetic fields may be utilized alone or in combination to separate the ions according to their mass-to-charge ratio. A sector field analyzer, a quadruple mass analyzer, an ion trap, a time-of-flight analyzer, and the like may be used as a mass analyzer.

High-Performance Liquid Chromatography (HPLC)

The HPLC method may be used to separate nonvolatile substances which may be difficult to analyze by gas chromatography based on their difference in physicochemical interactions with a stationary phase and a liquid mobile phase. This method may be used for qualitative and quantitative analysis of aldehydes in the air. Additionally, in HPLC, the target substances may be separated in the separation column based on their difference in reactivity with the stationary phase and the mobile phase.

When HPLC is employed for analysis of aldehydes existing in the air, a separation column in which a nonpolar stationary phase is chemically bonded to a support may be used. Separation may be achieved depending on difference in reactivity and solubility for the mobile phase and the stationary phase. In general, the method wherein a column containing a nonpolar stationary phase is used and a relatively polar sample eluent is used to separate target substances may be called reversed-phase HPLC.

The material of the tubing in the HPLC method may be stainless steel, polytetrafluoroethylene (PTFE), polyether ether ketone (PEEK), glass, or a similar material. Stainless steel may be advantageous due to being resistant to oxidation and corrosion. However, acid may cause damage and contamination to the tubing. Thus, when stainless steel or the like is used, the tubing should be washed with distilled water after use.

Often, an HPLC detector, capable of measuring absorption in the UV-visible (ultraviolet) region may be used. When incident light of a particular wavelength is emitted from a light source on the sample in the cell of the UV-visible detector, it may be absorbed by the sample. The detector may generate an electrical signal corresponding to the light absorbance, thus allowing quantitative analysis of the sample.

Hereinafter, the method for detecting the components contributing sweet odor according to the present invention is described. However, the application of the method is not limited to the described components.

Detection of Ammonia

The concentration of ammonia in the air may be measured as follows. After adding a phenol-sodium nitroprusside solution and a sodium hypochlorite solution to a sample solution to be analyzed, ammonia may be analyzed by measuring absorbance of indophenols formed from reaction with ammonium ion.

Detection of Methyl Mercaptan, Hydrogen Sulfide, Dimethyl Sulfide and Dimethyl Disulfide The concentration of the sulfur compounds in the air may be measured as follows. After sampling using a sample bag, analysis may be performed by cold trap-capillary GC and cold trap-packed column GC.

Cold Trap-Capillary GC and Cold Trap-Packed Column GC

The sulfur compound sample collected in the sample bag may be concentrated in a cold trap device (which may be maintained at about −183° C. or below using a refrigerant) and may be analyzed by GC after desorption. The measurement procedure may consist of sampling, concentration and sample injection to the separation column. A flame photometric detector (FPD), a pulsed flame photometric detector (PFPD), an atomic emission detector (AED), a sulfur chemiluminescence detector (SCD), a mass spectrometer (MS), and the like, capable of selectively detecting trace amount of sulfur compounds with substantially good linearity, may be used.

Electronic Device Cooling Cold Trap-Capillary GC

Sulfur compounds existing in the sample are concentrated at low temperature using a cold trap, desorbed at moderate temperature, and transferred into a syringe pump by the pressure of a carrier gas. The desorption occurs at moderate-to-low temperatures (e.g., about 100° C. or lower), not at high temperatures (e.g., above about 100° C.). The concentrated sample transferred to the syringe pump is injected into the separation column and analyzed by the detector. The cold-trapped sample may also be thermally desorbed and injected into the separation column.

Detection of Triethylamine

The concentration of triethylamine in the air may be measured as follows. After sampling using an impinger and acidic filter paper, analysis may be performed by cold trap-packed column GC and headspace-capillary column GC.

Detection of Acetaldehyde, Propionaldehyde, Butyraldehyde, n-Valeraldehyde and Isovaleraldehyde For simultaneous measurement of the concentration of acetaldehyde, propionaldehyde, butyraldehyde, n-valeraldehyde and isovaleraldehyde contributing to offensive odor, 2,4-dinitrophenylhydrazone (DNPH) derivatives of the aldehyde compounds may be formed and analyzed by HPLC and GC.

Dinitrophenylhydraziner (DNPH) Derivatization and HPLC/UV

DNPH derivatives formed by reacting carbonyl compounds with 2,4-dinitrophenylhydrazine (DNPH) are extracted with an acetonitrile solvent and analyzed by HPLC using a UV detector at 360 nm wavelength.

DNPH Derivatization and GC

DNPH derivatives formed by reacting carbonyl compounds with 2,4-DNPH may be extracted with an acetonitrile solvent and analyzed by GC after changing the solvent to ethyl acetate.

HPLC Instrument

The HPLC equipment for sample analysis may include: a sample injection device, a pump, a separation column and a detector (UV detector). The separation column may be a reversed-phase column (ODS column) to which a nonpolar adsorbent is coated allowing control of the mobile phase solvent according to the mixing ratio. The sample loop of the injection device may be about 20-100 μL depending on the sample concentration.

GC Instruments

A capillary separation column may be used for GC, and a flame ionization detector (FID), a nitrogen phosphorus detector (NPD) or a mass spectrometer may be used as the detector.

Detection of Styrene

Styrene may be sampled at the site boundary. After sampling using a solid sorbent tube, a canister or a sample bag, analysis may be performed by cold trap-GC and solid-phase microextraction (SPME)-GC.

Detection of Toluene, Xylene, Methyl Ethyl Ketone, Methyl Isobutyl Ketone, Butyl Acetate, Styrene and Isobutyl Alcohol The concentration of toluene, xylene, methyl ethyl ketone, methyl isobutyl ketone, butyl acetate, styrene and isobutyl alcohol, which are volatile compounds contributing to offensive odor, in the air may be simultaneously measured.

Toluene, xylene, methyl ethyl ketone, methyl isobutyl ketone, butyl acetate, styrene and isobutyl alcohol may be specified offensive odor substances. Sampling may be performed at the site boundary. The sample collected using a solid sorbent tube may be analyzed by GC after cold trapping and thermal desorption.

Detection of Propionic Acid, n-Butyric Acid, n-Valeric Acid and Isovaleric Acid

The concentration of the organic acids in the air may be measured as follows. After sampling using an alkaline-impregnated filter or by alkaline solution absorption, the collected sample may be pretreated by the headspace method to evaporate the organic acid components. Then, analysis may be carried out by GC.

In another aspect, the present invention provides a method for preparing a detected sweet odor composition from an air conditioner, including mixing two or more compounds selected from a group consisting of: hexanal, ethyl-2-methylbutyrate, heptanal, octanal, decanal, 1,3,5-trimethylbenzene, 1-methoxy-2-propanol, decane, 2-butoxyethanol, ethylbenzene, heptane, n-propylbenzene, 2-methylbenzene, n-undecane and n-tridecane.

In another aspect, the present invention provides a method for preparing a detected sweet odor composition from an air conditioner, including: mixing hexanal, ethyl-2-methylbutyrate, heptanal, octanal, decanal, 1,3,5-trimethylbenzene, 1-methoxy-2-propanol, decane, 2-butoxyethanol, ethylbenzene, heptane, n-propylbenzene, 2-methylbenzene, n-undecane and n-tridecane.

In an exemplary embodiment of the present invention, the method for preparing a detected sweet odor composition from an air conditioner according to the present invention may include mixing: about 0.0001-0.01 ppm of hexanal; about 0.0001-0.01 ppm of ethyl-2-methylbutyrate; about 0.00007-0.007 ppm of heptanal; about 0.0001-0.012 ppm of octanal; about 0.0001-0.013 ppm of decanal; about 0.0004-0.04 ppm of 1,3,5-trimethylbenzene; about 0.0003-0.03 ppm of 1-methoxy-2-propanol; about 0.0003-0.03 ppm of decane; about 0.001-0.1 ppm of 2-butoxyethanol; about 0.0002-0.03 ppm of ethylbenzene; about 0.0004-0.05 ppm of heptane; about 0.00008-0.01 ppm of n-propylbenzene; about 0.00008-0.08 ppm of 2-methyl pentane; about 0.0004-0.05 ppm of n-undecane; and about 0.0001-0.015 ppm of n-tridecane.

EXAMPLES

The present invention will be described in more detail through examples. The following examples are for illustrative purposes only and it will be apparent to those skilled in the art not that the scope of this invention is not limited by the examples.

Example 1

Sensory Test

1) Selection of Vehicle Model
Odor was sampled from the air conditioner of a vehicle model A.
2) Sensory Test Method
  i) Three out of the four air conditioner exhausts were sealed hermetically.
  ii) For sensory test and gas sampling, the exhaust at the left side of the driver seat was sealed hermetically using a glass tube and a vinyl bag.
  iii) The air conditioner was operated at level 2 under internal ventilation condition.
  iv) The panelist was asked to smell the sample in the glass tube and evaluate the intensity and type of odor.

Table 1 describes the level of odor according to intensity which was used as the standard of sensory test and evaluation after preparation of the mixtures for reproducing the detected odor in Examples 3 and 4.

TABLE 1

| Odor intensity | Level of odor |
| --- | --- |
| 5 | Irritating and intense odor |
| 4 | Strong odor |
| 3 | Weak but easily perceived odor |
| 2 | Perceived but slight odor |
| 1 | Almost unperceived odor |
| 0 | No odor |

Example 2

Sampling Procedure

1) Selection of vehicle model
Sample was taken from the same vehicle as in Example 1.
2) Sensory test method
  i) Three out of the four air conditioner exhausts were sealed hermetically.
  ii) The exhaust at the left side of the driver seat was sealed hermetically using a glass tube and a vinyl bag.
  iii) The opening of a 10-L PE sample bag was connected to the glass tube.
  iv) The air conditioner was operated at level 2 under internal ventilation condition and gas sample was taken.

Example 3

Sample Analysis

The sample taken in Example 2 was analyzed by absorption spectrophotometry, headspace-gas chromatography with flame ionization detector (HS-GC/FID), gas chromatography with flame photometric detector (GC/FPD), high-pressure liquid chromatography with ultraviolet detector (HPLC/UV), gas chromatography/mass spectrometry (GC/MSD) and headspace-gas chromatography/mass spectrometry (HS-GC/MS).

Table 2 shows the result of detecting compounds contributing to offensive odor from the sample.

TABLE 2

| Components | Concentration (ppm) |
| --- | --- |
| Acetone | 0.001229 |
| Isopropyl alcohol | 0.001193 |
| 1,4-Pentadiene | 0.000518 |
| Hexane, 3,3,4,4-tetrafluoro- | 0.001578 |
| Pentane, 2-methyl- | 0.00081 |
| Propane, 1-chloro-2-methyl- | 0.000648 |
| Oxetane, 2,3,4-trimethyl-, (2alpha,3alpha,4alpha-) | 0.008886 |
| 2-Propanol, 1-methoxy- | 0.002924 |
| Sulfide, allyl methyl | 0.000764 |
| Heptane | 0.000463 |
| Methyl isobutyl ketone (MIBK), 4-methyl | 0.001293 |
| Hexanal | 0.000892 |
| Heptane, 2,4-dimethyl- | 0.000413 |
| Cyclotrisiloxane, hexamethyl- | 0.001412 |
| Butanoic acid, 2-methyl-, ethyl ester | 0.001083 |
| 1-Methoxy-2-propyl acetate | 0.004621 |
| Ethylbenzene | 0.002585 |
| Heptanal | 0.00071 |
| Ethanol, 2-butoxy- | 0.010112 |
| Decane, 2,5,6-trimethyl- | 0.00116 |
| Hexanoic acid, methyl ester | 0.000553 |
| 2-Pentanol, 4,4-dimethyl- | 0.000478 |
| n-Propylbenzene | 0.000984 |
| Benzene, 1,3,5-trimethyl- | 0.004018 |
| Benzene, 1-ethyl-2-methyl- | 0.001571 |
| Propanoic acid, 3-ethoxy-, ethyl ester | 0.004018 |
| Pentanoic acid, 4-methyl-, ethyl ester | 0.001331 |
| Octanal | 0.001192 |
| Cyclotetrasiloxane, octamethyl- | 0.001048 |
| Decane | 0.003004 |
| 2-Propyl-1-pentanol | 0.006064 |
| yclohexene, 1-methyl-5-(1-methylethenyl)- | 0.002322 |
| Decane, 2-cyclohexyl- | 0.000898 |
| 2-(1-Hydroxyethyl)hydroxymethylbenzene | 0.001354 |
| Decane, 2,6,7-trimethyl- | 0.003584 |
| Hydroxylamine, O-decyl- | 0.001256 |
| Benzene, 4-ethyl-1,2-dimethyl- | 0.001108 |
| Nonanal | 0.005598 |
| 2-Propenoic acid, tridecyl ester | 0.000766 |
| Undecane | 0.004472 |
| Decane, 2,4,6-trimethyl- | 0.001445 |
| Benzene, 1,2,3,5-tetramethyl- | 0.00131 |
| Benzene, 1,2,4,5-tetramethyl- | 0.002078 |
| p-Trimethylsilyloxyphenyl-(trimethylsily | 0.014462 |
| 3-Hydroxymandelic acid, ethyl ester, di- | 0.000146 |
| Cyclohexanol, 5-methyl-2-(1-methylethyl) | 0.000756 |
| Decanal | 0.00131 |
| Tridecane | 0.001397 |
| 4-(Prop-2-enoyloxy)octane | 0.000268 |
| Trisiloxane, 1,1,1,5,5,5-hexamethyl-3,3- | 0.000405 |
| 3-Isopropoxy-1,1,1,7,7,7-hexamethyl-3,5, | 0.000867 |
| Pentadecane | 0.001138 |
| Silane, dimethyl(dimethyl(2-isopropylphenoxy)silyloxy)(2-isopropylphenoxy)- | 0.036299 |

10 L of sample was taken from the vehicle model A under the condition of air conditioner off.

Example 4

Preparation of Sweet Odor Composition

A sweet odor composition was prepared by mixing hexanal, ethyl-2-methylbutyrate, heptanal, octanal, decanal, 1,3,5-trimethylbenzene, 1-methoxy-2-propanol, decane, 2-butoxyethanol, ethylbenzene, heptane, n-propylbenzene, 2-methylpentane, n-undecane and n-tridecane according to the compositions described in Table 3.

TABLE 3

| Components | M.W. | Density | Conc. (ppm) | Bag volume (L) | Injection volume (mL) |
| --- | --- | --- | --- | --- | --- |
| Hexanal | 100.16 | 0.82 | 0.000892 | 6.0 | 0.44 |
| Ethyl-2-methylbutyrate (butanoic acid, 2-methyl-ethylester) | 130.18 | 0.87 | 0.001083 | 6.0 | 0.65 |
| Heptanal | 114.19 | 0.82 | 0.000710 | 6.0 | 0.40 |
| Octanal | 128.21 | 0.82 | 0.001192 | 6.0 | 0.75 |
| Decanal | 158.28 | 0.83 | 0.001310 | 6.0 | 1.00 |
| 1,3,5-Trimethylbenzene | 120.20 | 0.86 | 0.004018 | 6.0 | 2.25 |
| 1-Methoxy-2-propanol | 90.12 | 0.92 | 0.002924 | 6.0 | 1.15 |
| Decane | 142.28 | 0.73 | 0.003004 | 6.0 | 2.35 |
| 2-Butoxyethanol | 118.18 | 0.90 | 0.010112 | 6.0 | 5.32 |
| Ethylbenzene | 106.17 | 0.87 | 0.002585 | 6.0 | 1.27 |
| Heptane | 100.21 | 0.68 | 0.000463 | 6.0 | 0.27 |
| n-Propyl benzene | 120.2 | 0.862 | 0.000984 | 6.0 | 0.55 |
| 2-Methyl pentane, 99% | 86.18 | 0.65 | 0.000810 | 6.0 | 0.43 |
| n-Undecane, 99% | 156.31 | 0.74 | 0.004472 | 6.0 | 3.80 |
| n-Tridecane, 99% | 184.36 | 0.76 | 0.001397 | 6.0 | 1.37 |

The odor of the samples obtained from the air conditioner of the vehicle model A was sweet odor of intensity 3-4, as described in Table 4.

The odor of the sweet odor composition prepared from a combination of the aforementioned components was also sweet odor of intensity 3-4, similar to that from the air conditioner.

TABLE 4

| | | |
| --- | --- | --- |
| Odor from vehicle air conditioner | Intensity | 3-4 |
| | Characteristic | Sweet odor |
| Sweet odor composition prepared from detected compounds | Intensity | 3-4 |
| | Characteristic | Sweet odor |
| | Causative substance | Hydrocarbons |
| Note | Intensity | Similar |
| | Reproducibility | Reproducible |

The features and advantages of the present disclosure may be summarized as follows.

(i) Through the analysis method of the present invention, the compounds contributing to the detected sweet odor from an air conditioner may be identified and quantified.

(ii) The sweet odor may be reproduced from a combination of the compounds identified by the analysis method of the present invention.

(iii) The reproduced sweet odor may provide significant data required for development of an apparatus and a method for removing specific odor.

The present invention has been described in detail with reference to exemplary embodiments thereof. However, it will be appreciated by those skilled in the art that various changes and modifications may be made in these embodiments without departing from the principles and spirit of the invention, the scope of which is defined in the accompanying claims and their equivalents.

What is claimed is:

1. A detected sweet odor composition from an air conditioner, consisting of:
   0.0001-0.01 ppm of hexanal;
   0.0001-0.01 ppm of ethyl-2-methylbutyrate;
   0.00007-0.007 ppm of heptanal;
   0.0001-0.012 ppm of octanal;
   0.0001-0.013 ppm of decanal;
   0.0004-0.04 ppm of 1,3,5-trimethylbenzene;
   0.0003-0.03 ppm of 1-methoxy-2-propanol;

0.0003-0.03 ppm of decane;
0.001-0.1 ppm of 2-butoxyethanol;
0.0002-0.03 ppm of ethylbenzene;
0.0004-0.05 ppm of heptane;
0.00008-0.01 ppm of n-propylbenzene;
0.00008-0.08 ppm of 2-methylbenzene;
0.0004-0.05 ppm of n-undecane; and
0.0001-0.015 ppm of n-tridecane.

2. The detected sweet odor composition according to claim 1, wherein the air conditioner is used for hybrid vehicles, electric vehicles, combustion, or fuel cell vehicles.

3. A method for analyzing compounds contributing to sweet odor from an air conditioner, comprising:
   collecting a gas emitted from an air conditioner; and
   analyzing components of the gas,
   wherein the components analyzed in the gas and that contribute to the sweet odor consist of
   0.0001-0.01 ppm of hexanal;
   0.0001-0.01 ppm of ethyl-2-methylbutyrate;
   0.00007-0.007 ppm of heptanal;
   0.0001-0.012 ppm of octanal;
   0.0001-0.013 ppm of decanal;
   0.0004-0.04 ppm of 1,3,5-trimethylbenzene;
   0.0003-0.03 ppm of 1-methoxy-2-propanol;
   0.0003-0.03 ppm of decane;
   0.001-0.1 ppm of 2-butoxyethanol;
   0.0002-0.03 ppm of ethylbenzene;
   0.0004-0.05 ppm of heptane;
   0.00008-0.01 ppm of n-propylbenzene;
   0.00008-0.08 ppm of 2-methylbenzene;
   0.0004-0.05 ppm of n-undecane; and
   0.0001-0.015 ppm of n-tridecane.

4. The method according to claim 3, wherein the air conditioner is a vehicle air conditioner.

5. The method according to claim 3, wherein the concentration of the hexanal, ethyl-2-methylbutyrate, heptanal, octanal, decanal, 1,3,5-trimethylbenzene, 1-methoxy-2-propanol, decane, 2-butoxyethanol, ethylbenzene, heptane, n-propylbenzene, 2-methylbenzene, n-undecane and n-tridecane is measured.

6. The method according to claim 3, wherein the analysis of the components is performed by gas chromatography/mass spectrometry (GC/MS), gas chromatography with atomic emission detector (GC/AED), gas chromatography/flame ionization detection/olfactometry (GC/FID/olfactometry) or high-performance liquid chromatography (HPLC).

7. A method for preparing a detected sweet odor composition from an air conditioner comprising mixing compounds consisting of:
   0.0001-0.01 ppm of hexanal;
   0.0001-0.01 ppm of ethyl-2-methylbutyrate;
   0.00007-0.007 ppm of heptanal;
   0.0001-0.012 ppm of octanal;
   0.0001-0.013 ppm of decanal;
   0.0004-0.04 ppm of 1,3,5-trimethylbenzene;
   0.0003-0.03 ppm of 1-methoxy-2-propanol;
   0.0003-0.03 ppm of decane;
   0.001-0.1 ppm of 2-butoxyethanol;
   0.0002-0.03 ppm of ethylbenzene;
   0.0004-0.05 ppm of heptane;
   0.00008-0.01 ppm of n-propylbenzene;
   0.00008-0.08 ppm of 2-methylbenzene;
   0.0004-0.05 ppm of n-undecane; and
   0.0001-0.015 ppm of n-tridecane.

8. The method according to claim 7, wherein the air conditioner is used for hybrid vehicles, electric vehicles, combustion, or fuel cell vehicles.

* * * * *